United States Patent
Hadzic

(10) Patent No.: US 10,098,700 B2
(45) Date of Patent: Oct. 16, 2018

(54) NERVE BLOCK PROCEDURE DRAPE

(71) Applicant: Admir Hadzic, New York, NY (US)

(72) Inventor: Admir Hadzic, New York, NY (US)

( * ) Notice: Subject to any disclaimer, the term of this patent is extended or adjusted under 35 U.S.C. 154(b) by 257 days.

(21) Appl. No.: 14/699,107

(22) Filed: Apr. 29, 2015

(65) Prior Publication Data
US 2015/0305816 A1 Oct. 29, 2015

Related U.S. Application Data

(60) Provisional application No. 61/985,670, filed on Apr. 29, 2014.

(51) Int. Cl.
*A61B 46/00* (2016.01)
*A61B 19/10* (2006.01)
(Continued)

(52) U.S. Cl.
CPC .............. *A61B 19/10* (2013.01); *A61B 46/00* (2016.02); *A61B 46/23* (2016.02); *A61N 1/0502* (2013.01);
(Continued)

(58) Field of Classification Search
CPC ....... A61B 19/08; A61B 19/087; A61B 19/10; A61B 19/12; A61B 5/04; A61B 5/04001;
(Continued)

(56) References Cited

U.S. PATENT DOCUMENTS

| 4,040,418 | A | | 8/1977 | Collins |
| 5,042,981 | A | * | 8/1991 | Gross ..................... A61B 18/16 128/852 |

(Continued)

FOREIGN PATENT DOCUMENTS

| WO | 2009091678 A1 | 7/2009 |
| WO | 2012096828 A2 | 7/2012 |

OTHER PUBLICATIONS

"Surgical Site Signing and "Time Out": Issues of Compliance or Complacence", J Bone Joint Surg Am, Nov. 1, 2009, Geoffrey Johnston, BSc, MBA, MD; Lee Ekert, MD; Elliott Pally, BSc, MD; 12 pages.

(Continued)

*Primary Examiner* — Tarla R Patel
(74) *Attorney, Agent, or Firm* — Moreno Intellectual Property Law LLC

(57) ABSTRACT

In an embodiment, a device comprises a surgical drape having a fenestration formed therein and a nerve stimulator attached to an outward side of the surgical drape. One or more electrical conductors may also be attached to the drape and to the nerve stimulator. An electroconductive material may be arranged on a patient-facing side of the surgical drape. A connector may be attached to the surgical drape, which connector terminates an electrical conductor and is configured to permit attachment of an external nerve block needle. The attached nerve stimulator may be configured to provide a time-out indication. In another embodiment, the device comprises a surgical drape having at least one electrical conductor attached to the drape. At least one second connector may be attached to the surgical drape and configured to be in electrical communication with, and terminate, a second end of one or more electrical conductors.

10 Claims, 3 Drawing Sheets

(51) Int. Cl.
*A61N 1/05* (2006.01)
*A61B 46/23* (2016.01)
*A61B 5/04* (2006.01)
*A61N 1/34* (2006.01)

(52) U.S. Cl.
CPC ..... *A61B 5/04001* (2013.01); *A61B 2562/227* (2013.01); *A61N 2001/34* (2013.01)

(58) Field of Classification Search
CPC . A61B 5/0488; A61B 5/04882; A61B 5/0492; A61B 5/04888; A61B 5/04886; A61B 5/04884; A61B 2562/22; A61B 2562/221; A61B 2562/227; A61B 2019/084; A61B 46/00; A61B 46/20; A61B 46/23; A61B 46/27; A61B 46/30; A61B 46/40; A61B 46/10; A61B 46/13; A61B 2046/201; A61B 2046/205; A61B 2046/234; A61B 2046/236; A61N 2001/34
USPC .... 128/849–856; 607/149, 152, 46, 48, 142, 607/144
See application file for complete search history.

(56) References Cited

U.S. PATENT DOCUMENTS

| | | | |
|---|---|---|---|
| 5,074,316 A * | 12/1991 | Dowdy | A61B 46/00 128/849 |
| 5,830,151 A * | 11/1998 | Hadzic | A61N 1/36021 600/554 |
| 6,102,044 A * | 8/2000 | Naidyhorski | A61B 46/10 128/849 |
| 6,298,855 B1 | 10/2001 | Baird | |
| 6,382,212 B1 * | 5/2002 | Borchard | A61B 46/00 128/849 |
| 7,343,919 B2 | 3/2008 | Czajka et al. | |
| 7,555,347 B2 | 6/2009 | Loeb | |
| 7,770,583 B2 | 8/2010 | Harris et al. | |
| 7,886,742 B2 | 2/2011 | Haines et al. | |
| 8,371,306 B2 | 2/2013 | Haines et al. | |
| 2003/0060831 A1 * | 3/2003 | Bonutti | A41D 19/0157 606/86 R |
| 2003/0184081 A1 | 10/2003 | Carlson, II | |
| 2003/0187458 A1 | 10/2003 | Carlson, II | |
| 2004/0118410 A1 | 6/2004 | Griesbach, III et al. | |
| 2005/0245969 A1 * | 11/2005 | Loeb | A61N 1/05 607/2 |
| 2009/0178685 A1 | 7/2009 | Haines et al. | |
| 2009/0210029 A1 * | 8/2009 | Tsui | A61B 5/053 607/46 |
| 2011/0107494 A1 | 5/2011 | Haines | |
| 2012/0232389 A1 | 9/2012 | Guzman | |
| 2013/0087156 A1 | 4/2013 | Sloth et al. | |
| 2013/0165904 A1 * | 6/2013 | Hadzic | A61M 5/486 604/512 |
| 2013/0186413 A1 | 7/2013 | Haines et al. | |

OTHER PUBLICATIONS

International Search Report and Written Opinion, filed in PCT/US2015/028161, dated Jul. 27, 2015, 13 pages.

Brochure entitled "Pajunk MultiStim Switch and MultiStim Sensor," 12 pages (accessed Nov. 7, 2017 at: https://www.pajunkusa.com/pdf/MultiStim_Switch_Sensor_GB.pdf).

Brochure entitled "VYGON Locoplex, Techniplex & Plexygon," 6 pages (accessed Nov. 7, 2017 at: http://www.vuygon.co.uk/pdf/upload/PLexygon_Locoplex_web.pdf).

Extended European Search Report fo European Patent Application No. 1578063.6, dated Nov. 15, 2017, 6 pages.

* cited by examiner

NERVE BLOCK PROCEDURE DRAPE

CROSS-REFERENCE TO RELATED APPLICATION

The instant application claims the benefit of Provisional U.S. patent application Ser. No. 61/985,670 entitled "Medical Drape" and filed Apr. 29, 2014, the teachings of which are incorporated herein by this reference.

FIELD

The instant disclosure relates generally to medical drapes and, in particular, to a nerve block procedure drape incorporating various additional features useful in nerve stimulation and/or regional anesthesia procedures.

BACKGROUND

Nerve stimulation is a commonly used method for localizing nerves before the injection of a local anesthetic, i.e., in regional anesthesia. More particularly, electrical nerve stimulation is used to obtain a defined response (e.g., evoked motor response (EMR), muscle twitch or patient sensation) to accurately locate a peripheral nerve or nerve plexus with a needle. The needle is thereafter used to inject anesthetic in close proximity to the nerve to block nerve conduction and provide a sensory and/or motor block for surgery and/or, eventually, analgesia for pain management. Such procedures require sterile conditions. To accomplish sterile conditions, clinicians typically use a disposable, fenestrated or non-fenestrated sheet/drape. The sterile drapes in current use, however, are not ideally adjusted to a particular medical need in the field of regional anesthesia and nerve blocks.

The electrical aspects of nerve stimulation as applied to regional anesthesia can give rise to particular challenges. For example, during performance of peripheral nerve block procedures, many clinicians utilize a peripheral nerve stimulator. A nerve stimulator is a valuable tool during application of nerve blocks to identify the nerve(s) and decrease the risk of nerve injury by an advancing needle. However, existing surgical drapes do not allow for a secure, sterile and convenient application of nerve stimulation during such procedures. Further, prior to a procedure, clinicians must locate a peripheral nerve stimulator, and bring/position the stimulator to the patient's bed-side in order to use it during the procedure. When such nerve stimulator is misplaced, the clinicians often need to perform the procedure without reliance on nerve stimulation, therefore compromising on patient safety. Additionally, such stimulators require maintenance, battery change, calibration and test for accuracy and electrical safety by biomedical electric technicians or engineers. Taken together, this makes the use of currently available, stand-alone, reusable nerve stimulators cumbersome and time-inefficient.

Further, the use of electrical nerve stimulators requires that one lead of the nerve stimulator be connected to the patient and the other to the stimulating needle. The nerve stimulator leads (cables) can easily become detached or disconnected during the procedure and result in an open electrical circuit and consequently, failure to electro-localize or detect a hazardous needle-nerve relationship. In addition, the nerve stimulator leads (cables) are typically of a multiple-use type and not sterile. Therefore, the presence of non-sterile electrical leads on the field can contaminate the sterile field during the procedure. In addition, the return electrode (+) is connected to the lead from the nerve stimulator and patients skin via an adhesive, such as an electroconductive gel. Most typically, electrocardiogram (EKG/ECG) electrodes are used for this purpose. However, it is common occurrence that this electrode gets disconnected during procedures due to dryness of the patient's skin or greasy/slick skin conditions after application of moisturizing lotion, etc. Similar problems with the risk of disconnect occur when gel on an EKG leads becomes dry/desiccated causing a faulty connection and/or poor adhesion to the skin. Although many nerve stimulators incorporate some means of detecting the electrical disconnect and resulting open circuit, this may not be easily detected in a busy, noisy, clinical environment, yet, the electrical failure may lead to wrong or hazardous placement of the needle too close or into the nerves and a consequent nerve injury. Further still, application of a ground electrode is another step in the procedure process and therefore increases the likelihood of error.

Thus, it would be advantageous to provide nerve block procedure drapes that overcome these shortcomings.

SUMMARY

The instant disclosure describes various embodiments of a nerve block procedure drape. In a first embodiment, the nerve block procedure drape comprises a surgical drape having a fenestration formed therein and a nerve stimulator attached to an outward side of the surgical drape. The surgical drape may be formed of a substantially transparent material. One or more electrical conductors may also be attached to the drape. In the first embodiment, the one or more electrical conductors are coupled to the nerve stimulator. An electroconductive material may be arranged on a patient-facing side of the surgical drape, wherein a first conductor of the at least one conductor is in electrical communication with the electroconductive material. The electroconductive material may be placed in substantial proximity to the fenestration and, in a further embodiment, is arranged to surround the fenestration. A removable layer may be provided such that the electroconductive material is disposed between the patient-facing side of the surgical drape and the removable layer. A connector may be attached to the surgical drape, which connector terminates an electrical conductor of the at least one electrical conductor and is configured to permit attachment of an external nerve block needle. The attached nerve stimulator may be configured to provide a time-out indication and, in an embodiment, the time-out indication is provided by a display of the nerve stimulator. One or more pockets may be provided on the surgical drape, which pocket(s) may also be fabricated from a substantially transparent material.

In a second embodiment, the nerve block procedure drape comprises a surgical drape having at least one electrical conductor attached to the drape. In this embodiment, a first connector may be attached to the outward side of the surgical drape, and a first end of a first conductor of the at least one conductor may be terminated by the first connector. The first connector may be attached to the drape in proximity to the fenestration, and in a further embodiment, the first connector may be configured to permit attachment of an external nerve block needle. At least one second connector may be attached to the surgical drape and configured to be in electrical communication with, and terminate, a second end of one or more second electrical conductors. The at least one second connector may be attached to the surgical drape in proximity to an edge of the surgical drape and, in an embodiment, is further configured to establish electrical communication with an external nerve stimulator. Electroconductive material and a removable layer may be provided in substantially the same manner as the first embodiment, with one of the at least one electrical connectors operatively connected (i.e., in electrical communication with) the electroconductive material.

BRIEF DESCRIPTION OF THE DRAWINGS

The features described in this disclosure are set forth with particularity in the appended claims. These features and attendant advantages will become apparent from consideration of the following detailed description, taken in conjunction with the accompanying drawings. One or more embodiments are now described, by way of example only, with reference to the accompanying drawings wherein like reference numerals represent like elements and in which:

DETAILED DESCRIPTION OF THE PRESENT EMBODIMENTS

Figure 1:
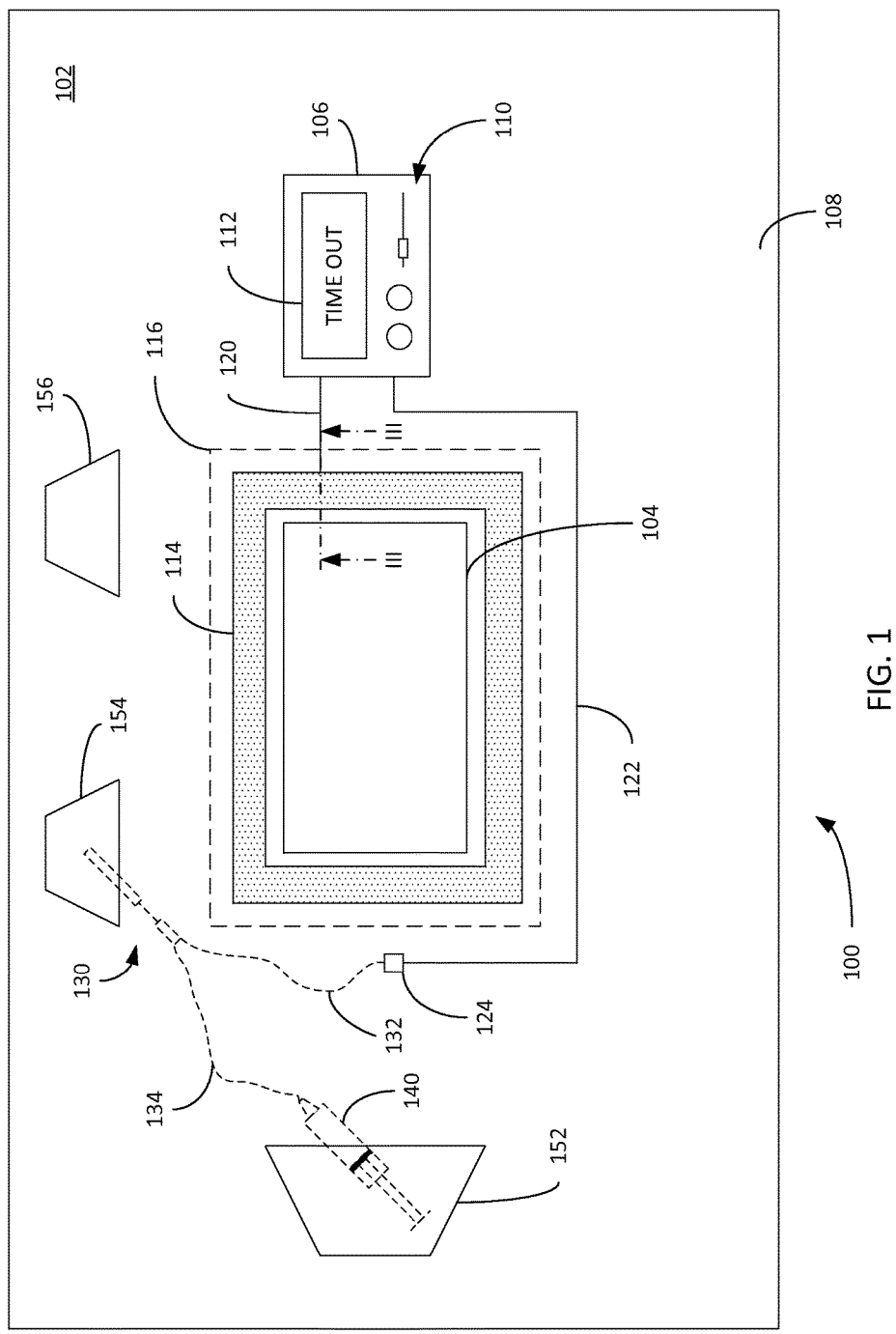
FIG. 1 is a top-down view of a nerve block procedure drape comprising a surgical drape and a nerve stimulator in accordance with a first embodiment of the instant disclosure.

Referring now to FIG. 1, a nerve block procedure drape 100 in accordance with a first embodiment is illustrated. Generally, the nerve block procedure drape 100 is manufactured in accordance with the so-called Good Manufacturing Practice (GMP) regulations promulgated by the U.S. Food and Drug Administration, particularly to ensure sterility of the nerve block procedure drape 100. In the illustrated embodiment, the nerve block procedure drape 100 comprises a surgical drape 102 having a fenestration 104 formed therein. The surgical drape 102 has an outward side 108 that is opposite to a patient-facing side 302 (see FIG. 3). The outward side 108 is configured to be exposed to the (potentially non-sterile) environment in which a nerve block procedure is being performed, whereas the patient-facing side 302 is configured to be placed, when in use with a patient, facing toward the patient. In an embodiment, the surgical drape 102 is manufactured by a substantially transparent material such as a suitable plastic material (e.g., polyvinyl chloride (PVC)) that permits a clinician to observe the patient therethrough. In this manner, the clinician (particularly when performing nerve stimulation in regional anesthesia procedures) can observe the reaction of tissues to the procedure being performed.

Although a single fenestration is illustrated in FIG. 1, this is not a requirement as a greater number of fenestrations could be formed in the surgical drape 102. Furthermore, the fenestration 104 may be formed to have any desired shape or size as a matter of design choice. In this first embodiment, the nerve block procedure drape 100 further comprises a nerve stimulator 106, as shown. The nerve stimulator 106 may comprise the same functional components and capabilities of any of a number of commercially available nerve stimulators, examples of which include the "STIMUPLEX" HNS 12 nerve stimulator available from B. Braun Melsungen AG, the MultiStim SENSOR nerve stimulator available from Pajunk GmbH or the Plexygon nerve stimulator provided by Vygon SA. In this embodiment, the nerve stimulator 106 is configured to have as small a form factor as possible to permit attachment of the nerve stimulator 106 to the outward side 108 of the surgical drape 102. Additionally, because the device 100 is generally a disposable item, it is desirable for the nerve stimulator 106 to be manufactured for disposable use, which may include the use of environmentally friendly batteries, relatively inexpensive materials, etc. The nerve stimulator 106 may be attached to the surgical drape using a suitable glue or adhesive, placed within a pocket (not shown) also formed on the outward side 108 of the surgical drape 102 or using any other means known to those having skill in the art. As noted, the nerve stimulator 106 is capable of providing stimulating currents and waveforms using controls 110 known in the art. In short, the nerve stimulator 106 is capable of providing the same functionality as other, currently available nerve stimulators in the market.

In an embodiment, the nerve stimulator 106 is configured to provide a time-out indication when the nerve block procedure drape 100 is first deployed. As known in the art, a "time-out" indicator comprises some form of a visually perceptible reminder to the clinician to perform routine and basic checks to ensure that the proper procedure is being done on the correct patient. Thus, the nerve stimulator 106 may be equipped with a mechanism capable of providing a visual indication of to help remind the clinician of the need to perform a time-out procedure. For example, the nerve stimulator 106 may be equipped with a low power consumption light emitting diode (LED), liquid-crystal display (LCD) or the like. So equipped, the nerve stimulator 106 may be programmed at the time of manufacture (via suitable embedded software programming, hardwired logic or circuitry, as known in the art) to periodically and continuously cause the LED to flash until such time as the nerve stimulator is turned on for the first time. Thus, when the nerve block procedure drape 100 is unfolded for application to the patient, the clinician is able to observe the flashing indicator reminding him/her to perform the time-out procedure. Alternatively, such flashing could be programmed to occur the first time the nerve stimulator 106 is turned on. Regardless, the flashing LED thereby serves to remind the clinician of the time-out procedure (and may also provide the beneficial effect of serving as an indication that the nerve stimulator 106 remains operative). In another embodiment, illustrated in FIG. 1, the nerve stimulator 106 may comprise a suitable built-in display 112 that is configured to initially display the phrase "Time Out" (or similarly indicative phrase) in substantially the same manner as the LED embodiment, i.e., before or after initial turning on of the nerve stimulator 106. Furthermore, the built-in display 112 can also display various additional safety and check list information, related to patient monitoring or medications dosing. In yet another embodiment, known circuitry may be provided in the nerve stimulator 106 such that it is able to detect the attachment of an electrode (e.g., an external nerve block needle) to the nerve stimulator 106, thereby initiating the display of the time-out indicia as described above.

Figure 3:
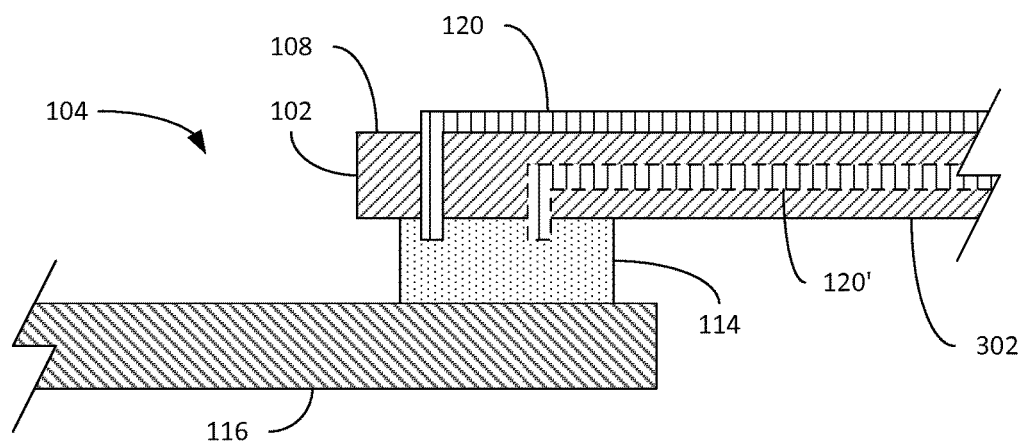
FIG. 3 is a cross-sectional view of a portion of a surgical drape in proximity to a fenestration formed in the surgical drape in accordance with the instant disclosure.

With reference to FIGS. 1 and 3, the nerve block procedure drape 100 may be further provided with an electroconductive material 114, such as electoconductive gel of the type typically used in EKG electrodes and the like, on the patient-facing side 302 of the surgical drape 102. In addition to being electrically conductive, the electroconductive material 114 is selected to provide a suitable degree of adhesion to human skin such that the electroconductive material 114 helps secure the surgical drape 102 to the patient and maintain the configuration of the surgical drape 102 as it is deployed on the patient. Generally, the electroconductive material 114 can be provided at single point at virtually any point on the surgical drape 102, thereby providing a conductive path through the patient's tissues and skin to complete an electrical circuit when performing nerve stimulation. To the extent that the fenestration 104 provides a window through which the surgical procedure may be performed, it is often desirable to place the electroconductive material 114 in proximity to the fenestration 104, as opposed to, for example, the most distal points of the surgical drape 102 relative to the fenestration 104. In a presently preferred embodiment, the electroconductive material 114 surrounds the fenestration 104, as illustrated in FIG. 1, thereby maximizing the likelihood of a secure and electrically reliable connection with the patient's skin.

Figure 2:
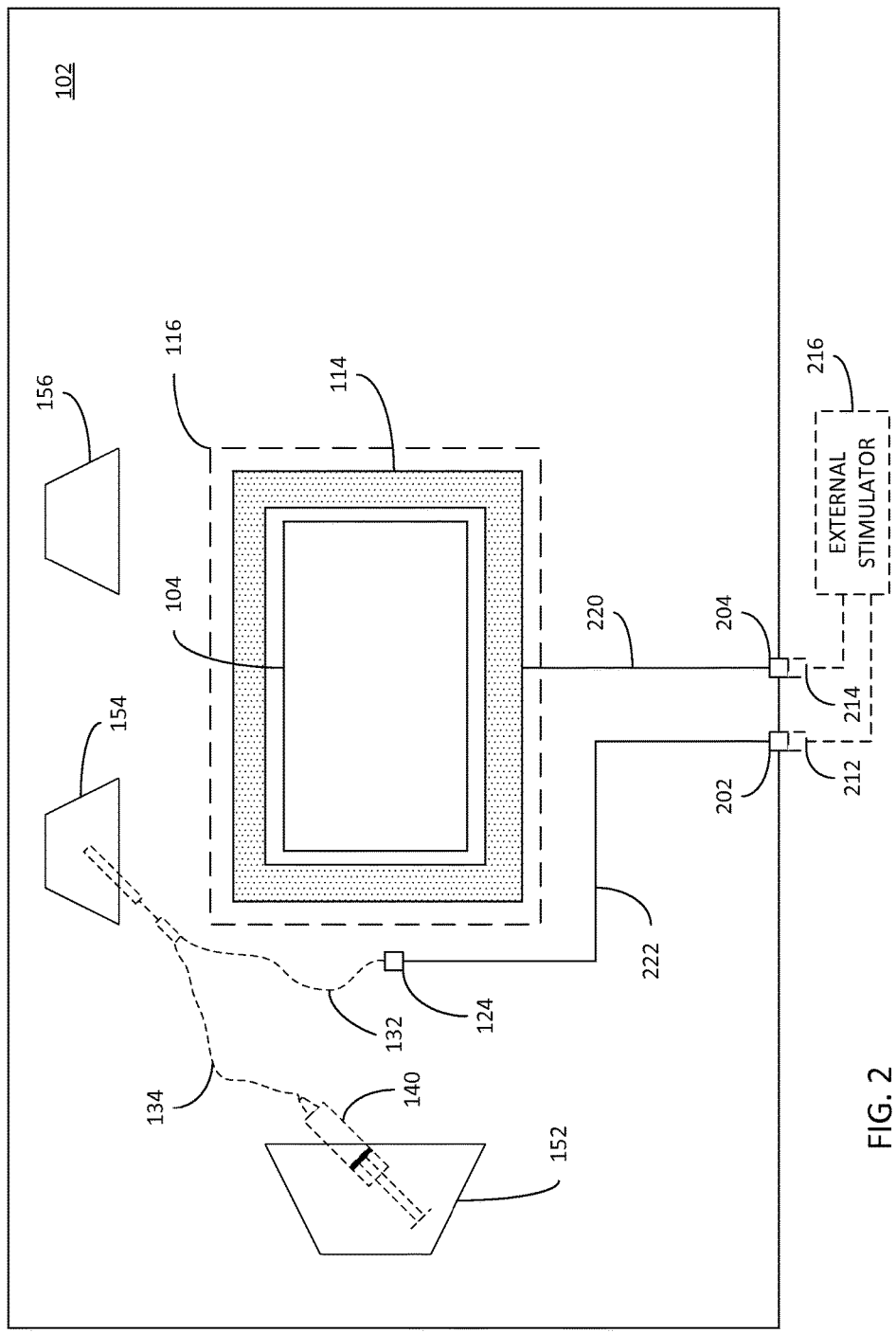
FIG. 2 is a top-down view of a nerve block procedure drape comprising a surgical drape and at least one electrical conductor in accordance with a first embodiment of the instant disclosure.

As best shown in FIG. 3, a removable layer 116 may be provided such that the electroconductive material 114 is disposed between the surgical drape 102 and the removable layer 116. (It is noted that the dimensions shown in FIGS. 1-3 are not necessarily to scale and are shown for illustrative purposes only.) Once again, as illustrated in FIG. 3, the electroconductive material 114 is placed in proximity to the fenestration 104. In an embodiment, the removable layer 116 may be manufactured from a suitable, disposable material such as paper or plastic. Further, a side of the removable layer 116 facing the electroconductive material 114 may presently a comparatively low degree of adhesion with the electroconductive material 114 as compared to the degree of adhesion between the surgical drape 102 and the electroconductive material 114. In this manner, the removable layer 116 may be placed as a protective barrier over the electroconductive material 114 at the time of manufacture and remain in this position until removed by a clinician during use with a patient. Additionally, the removable layer 116 may also contain information relating to nerve block documentation or reminders to practitioners to perform a time-out check list before performing the procedure. In one embodiment, the removable layer 116 may comprise a lamination of sub-layers, including a further removable sub-layer comprising the check list (such as an adhesive-backed paper or other suitable material) that can be subsequently affixed into patient's medical record.

Referring once again to FIG. 1, one or more electrical conductors 120, 122 may be attached to the surgical drape 102. The conductor(s) 120, 122 may be formed of substantially flexible wires or the like that may flex and bend in conjunction with the surgical drape 102. Such wires are preferably insulated and attached to the surgical drape 102 via an appropriate glue or adhesive. Examples of this are illustrated in FIG. 3, which illustrate a cross-sectional view taken along sectional line III-III in FIG. 1. In an illustrated embodiment, the conductor(s) 120 may be attached to the outward side 108 of the surgical drape 102, though it may also be possible to attach the conductors to the patient-facing side 302 of the surgical drape 102. In an alternative embodiment, the surgical drape 102 may comprise a number of laminated layers, with the conductor(s) 120' residing between constituent layers of the surgical drape 102. Regardless, FIG. 3 also illustrates, in this case, the electrical connection established between the conductor 120, 120' and the electroconductive material 114. In the illustrated embodiment, the conductor 120, 120' extends through the thickness of the surgical drape 102 to make contact with the electroconductive material 114. Those having skill in the art will appreciate that other arrangements may be employed to establish the electrical connection between the conductor 120, 120' and the electroconductive material 114.

In the embodiment shown in FIG. 1, the conductors 120, 122 are coupled to the nerve stimulator 106, particularly to an output of an electrical nerve stimulation signal. A first electrical conductor 120 is in electrical communication with the electroconductive material 114, whereas an end of a second conductor 122 is terminated by, and in electrical communication with, a connector 124. For example, in the case where the second conductor 122 is an insulated wire attached to the surgical drape 102 via an adhesive, the connector 124 may be operatively connected to the second conductor 122 using conventional means, and then attached to the drape in a similar manner as the second conductor 122. Although the connector 124 is illustrated as having a particular placement on the surgical drape 102 relative to the fenestration 104, this is not a requirement as the connector 124 may be placed at virtually any point along the surgical drape 102 as a matter of design choice. In an embodiment, the connector 124 is configured to permit the attachment of an external nerve block needle 130 via an electrical lead 132 having a mating connector (not shown). When the needle 130 is inserted in the patient, the combination of the electrical lead 132, needle 130, the patient's tissues and skin, the electroconductive material 114, the conductors 120, 122 and the connector 124 provide a complete electrical circuit for the application of suitable stimulation signals to the tissue. As known in the art of regional anesthesia, the nerve block needle 130 can also be coupled to a syringe 140 or other fluid delivery device via suitable tubing 134.

In an alternative to the particular embodiment shown in FIG. 1, the second electrical conductor 122 is not provided in the surgical drape; only the first electrical conductor 120 is provided as shown and described above. In this case, the connector 124 would also not be required. Rather, in this alternative, an electrical lead typically provided with commercially available nerve stimulator needles is attached directly to the nerve stimulator 106, thereby obviating the need for the second electrical conductor 122 and connector 124.

Finally, as shown in FIG. 1, one or more pockets 152-156 may be provided on the outward side 108 of the surgical drape 102. Preferably, the pockets 152-156, which may be glued or otherwise adhered to surgical drape 102, are fabricated from a substantially transparent material, thereby allowing a clinician to quickly ascertain the contents (if any) of each pocket and/or to further provide visual access to the patient's tissues. As shown, the pockets 152 may be of different sizes and have various positions and orientations relative to the surgical drape 102 as a matter of design choice. The pockets 152-156 are preferably sized to permit the storage of equipment or supplies commonly used in the relevant surgical procedures, e.g., the needles 130 or syringes 140 used in regional anesthesia.

Referring now to FIG. 2, a second embodiment in accordance with the instant disclosure is illustrated. In particular, the embodiment of FIG. 2 is substantially similar to the embodiment of FIG. 1 with the exception that the nerve stimulator 106 is not provided. Instead, one or more second connectors 202, 204 are provided to terminate and electrically communicate with second ends of each of the conductors 220, 222 that are attached to the surgical drape 102. The second connectors 202, 204 are configured to mate with complementary connectors 212, 214 that permit electrical communication with an external nerve stimulator 216. The second connectors 202, 204 may be positioned at any point along the surgical drape 102. However, as shown, it may be desirable to locate the second connectors 202, 204 in proximity to an edge of the surgical drape 102. In this manner, the likelihood of leads from the external stimulator 216 entering into the surgical field established by the fenestration 104 are minimized.

It should be noted that, while the teachings above have been presented in the context of a nerve block procedure drape for use in, for example, nerve stimulation as applied to regional anesthesia, the instant disclosure is not necessarily limited in this regard. Indeed, it is contemplated that the devices taught herein could be used in any procedure incorporating electrical stimulation of nerves, or any other procedure that may benefit from the above-described features.

While particular preferred embodiments have been shown and described, those skilled in the art will appreciate that changes and modifications may be made without departing from the instant teachings. It is therefore contemplated that any and all modifications, variations or equivalents of the above-described teachings fall within the scope of the basic underlying principles disclosed above and claimed herein.

What is claimed is:

1. An apparatus for use in a nerve block procedure, comprising:
    a surgical drape having a patient-facing side and an outward side opposite the patient-facing side, and further comprising a fenestration formed therein;
    a nerve stimulator directly attached to the outward side of the surgical drape;
    at least one electrical conductor attached to the drape and coupled to the nerve stimulator; and
    electroconductive material on the patient-facing side of the surgical drape, wherein a first electrical conductor of the at least one electrical conductor is operatively connected to the electroconductive material.

2. The apparatus of claim 1 wherein the electroconductive material is disposed in proximity to the fenestration.

3. The apparatus of claim 1 wherein the electroconductive material is disposed surrounding the fenestration.

4. The apparatus of claim 1 further comprising:
    a removable layer, wherein the electroconductive material is disposed between the patient-facing side of the surgical drape and the removable layer.

5. The apparatus of claim 1, wherein an electrical conductor of the at least one electrical conductor terminates in a connector configured to permit the attachment of an external nerve block needle.

6. The apparatus of claim 1, wherein the nerve stimulator is configured to provide a time-out indication.

7. The apparatus of claim 1, wherein the nerve stimulator comprises a display screen, and the nerve stimulator is configured to display the time-out indication on the display screen.

8. The apparatus of claim 1, wherein material forming the surgical drape is a transparent material.

9. The apparatus of claim 1, further comprising:
    at least one pocket formed on the outward side of the surgical drape.

10. The apparatus of claim 9, wherein material forming the at least one pocket is a transparent material.

* * * * *